(12) United States Patent
Silver

(10) Patent No.: US 6,542,570 B1
(45) Date of Patent: Apr. 1, 2003

(54) METHOD AND SYSTEM FOR RECONSTRUCTING COMPUTED TOMOGRAPHY IMAGES USING REDUNDANT DATA

(75) Inventor: Michael D. Silver, Northbrook, IL (US)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/549,562

(22) Filed: Apr. 14, 2000

(51) Int. Cl.[7] .................................................. A61B 6/03
(52) U.S. Cl. ........................................ 378/4; 378/901
(58) Field of Search .............................. 378/4, 15, 901, 378/19, 131

(56) References Cited

U.S. PATENT DOCUMENTS

| | | | | |
|---|---|---|---|---|
| 5,270,923 A | * | 12/1993 | King et al. ................. 382/131 |
| 5,805,659 A | * | 9/1998 | Tam ............................ 378/15 |
| 6,038,282 A | * | 3/2000 | Wiesent et al. ............. 378/62 |
| 6,130,929 A | * | 10/2000 | Saha ............................ 378/4 |
| 6,185,271 B1 | * | 2/2001 | Kinsinger .................... 378/19 |
| 6,324,247 B1 | * | 11/2001 | Besson ........................ 378/15 |

* cited by examiner

Primary Examiner—Drew A. Dunn
Assistant Examiner—Chih-Cheng Glen Kao
(74) Attorney, Agent, or Firm—Oblon, Spivak, McClelland, Maier & Neustadt, P.C.

(57) ABSTRACT

A method and system for reconstructing an x-ray image from a partial orbit through the use of a "virtual" fan angle. The virtual fan angle is determined based upon the range of angular positions spanned by a source in a CT instrument or a selected smaller angle. Exposure data is obtained and he virtual fan angle is used to weight the exposure data. Image reconstruction can then proceed using the weighted exposure data. The described methods and system also function for data collected over a complete orbit.

27 Claims, 11 Drawing Sheets

METHOD AND SYSTEM FOR RECONSTRUCTING COMPUTED TOMOGRAPHY IMAGES USING REDUNDANT DATA

BACKGROUND OF THE INVENTION

1. Field of the Invention

The present invention relates to a method and system for image reconstruction in fan-or cone-beam X-ray computed tomography and, in particular, to a method and system for reconstructing images using weighting coefficients to weight exposure data.

2. Discussion of the Background

Fan- and cone-beam computed tomography (CT) reconstructs the interior of an object of interest or patient from one-dimensional and two-dimensional projections, respectively, of transmitted x-rays through the object of interest or patient. An x-ray source and an x-ray detector are arranged in a number of different positions so that x-rays transmitted through the object of interest are received at the detector. The detector, either alone or in conjunction with other devices, generates image data for each position of the source and/or detector. The image data is then stored, manipulated, and/or analyzed to reconstruct the interior of the object. In a fan-beam system, the detector forms a linear array of x-ray sensing elements while in a cone-beam system, the detector forms an array of x-ray sensing elements.

The classical path of the x-ray source and detector is along a complete circular orbit, i.e. 360°, about the object of interest. The source and detector are mechanically joined so as to maintain a constant separation distance and position relative to each other and then revolved around the object.

As shown in FIG. 1, an X-ray source S emits either a cone- or a fan-beam of X-rays toward a detector D. The X-rays emitted by source S are incident upon a three-dimensional object of interest (not shown) such as a calibration phantom, a patient, a test object, or other article of interest. At least a portion of the X-rays generated at point source S pass through or around the object and are received at the detector D. The source S and the detector D are fixed relative to one another and revolve in a substantially circular orbit about an axis A in, for example, a C-arm gantry or ring gantry device. The angular position of the X-ray source S is illustrated here as the angle $\beta$ relative to an arbitrary half-line L that terminates at the rotation axis A.

Several disadvantages of complete circular orbits of the source and detector about the object arise due to the nature of the complete orbit itself. Electrical leads must be capable of circumscribing one or more complete revolutions about the object of interest. In medical CT, since the patient must be contained within the orbiting detector and source, access to the patient by medical personnel is hindered. Furthermore, many patients dislike being enclosed within the CT mechanism for the extended times necessary to gather sufficient image data for meaningful reconstruction.

In fan-beam CT, the detector D is a substantially linear array of detector elements typically in arc form on the array source. In cone-beam CT, detector D is an area array of detector elements. Curved line and curved surface arrays of detector elements are also suitable for use as detector element D. In all of these cases, detector element D will have a cross sectional area with a width W in a plane orthogonal to the axis of rotation A. In this particular embodiment, the midpoint of the width of a linear array detector D is substantially positioned at a line N passing through the center of the source S and the axis A.

The angle $\gamma$ illustrated in FIG. 1 describes the angle of a ray O joining the source S and one element selected from the matrix of elements that constitutes the detector D. In fan-beam CT, the angle $\gamma_m$ describes the rays M with the largest (maximum) angle relative to the line N, where the ray M is emitted by the source S and received by the detector D. The physical limit on ray M and hence angle $\gamma_m$ can arise due to, for example, the finite length of the detector D (as illustrated), collimation of the source emission (not shown), or the non-omnidirectional emission of X-rays by the source S (also not shown). In FIG. 1 with the midpoint of the cross-sectional area of detector D located at line N, the angle $\gamma_m$ on one side of the axis is equal and opposite to angle $\gamma_m$ on the other side of the axis. Shifting the detector D relative to line N will change this relationship between the two $\gamma_m$'s and can be accounted for using traditional geometric rules.

FIGS. 2a–c illustrate three example rays $O_a$, $O_b$, and $O_c$ over which the same x-ray transmittance is measured at two different angular positions of the source $\beta$ relative to an arbitrary half-line L and fan beam angles $\gamma$. For illustrative purposes, the first angular positions of the source $\beta$ is equal to zero in all three examples. In FIG. 2a, ray $O_a$ is the first ray sampled twice, while FIGS. 2b and 2c show respective rays $O_b$ and $O_c$ that are sampled twice at other positions.

In recent years, there has been an attempt to implement fan- and cone-beam CT on gantries that only revolve around a portion of the object or patient during imaging. Such partial orbits are capable of providing complete image data for reconstruction of the interior of an object since many views in a complete circular orbit are redundant, i.e., the image data provide little or no new information. For example, if the object of interest is immobile and the system is ideal (i.e., no noise), switching the location of the source and detector will provide no new information along the ray through the axis even though image data from a second view has been collected.

The advantages of such partial orbits include easier and less expensive mechanical realization, providing access to a patient during medical imaging and enabling supporting mechanisms for the source and detector that do not require complete enclosure of the patient. Also, it allows the use of x-ray imaging and primarily designed for non-CT imaging application to also be used to obtain a CT-image for special needs.

A method for reconstruction of one particular partial orbit, namely an orbit that covers the "minimal complete data set" has been described by Dennis Parker ("Optimal Short Scan Convolution Reconstruction for Fanbeam CT," Med. Phys. 9, 254–257, 1982) which is incorporated herein by reference. The "minimal complete data set" is the collection of equally-spaced projection image data that can be used in conventional, convolution type, reconstruction methods. The "minimal complete data set" spans more than one half of a complete orbit. Namely, it spans 180° plus the maximum fan angle $2\gamma_m$, where the maximum channel angle $\gamma_m$ is the largest angle of a ray emitted by the X-ray source that is received at the (substantially two- or three-dimensional) X-ray detector relative to the ray emitted from the source that passes through the axis of rotation of the X-ray source and detector. FIG. 1 schematically illustrates this and other terminology used to describe the current invention.

One disadvantage with the use of such a "minimal complete data set" orbit lies in the fact that certain rays are sampled twice as often as other rays. In other words, certain image data is collected twice as often as other image data and are redundant. Illustrative examples are illustrated diagrammatically in FIGS. 2a–c. This can be better illustrated in FIG. 3, where the image data is represented in Radon space. The horizontal axis in FIG. 3 corresponds to the channel angle γ, the vertical axis corresponds to the angular position β of the x-ray source, and, in an actual Radon space representation of a collection of x-ray image data, the grey level of each point in Radon space would correspond to the line integral of the x-ray transmittance along the particular ray defined by the fan angle γ and the angular position of the source β. FIG. 3. indicates the angular positions of the source and the channel angles for rays that are sampled shown by shaded regions during the collection of a "minimal complete data set" partial orbit (including those rays illustrated in FIGS. 2a–2c). Such Radon space representations of image data are well-known in the art, and a more complete explanation of these representations can be found in several textbooks including "Image Reconstruction From Projections: The Fundamentals of Computerized Tomography" by Gabor T. Herman, Academic Press, New York, 1980, p. 36–39 and 161–165, the entire contents of which is incorporated herein by reference. In general, the line integrals along the rays p(β,γ) and p(π+β+2γ,−γ) are equivalent. When the total collection of image data is used to reconstruct the interior of an object, the twice collected image data distorts the appearance of the final image and yields poor quality images.

Various methods and devices for solving this problem with the minimal complete data set have been proposed and implemented. The image data can be rebinned into parallel ray data sets and then analyzed, but this requires further computational effort and time. Naparstek described several alternate methods (IEEE Trans. Nucl. Sci. NS-27, p. 1112 ff., 1980, which is hereby incorporated by reference) that, however, provided inadequate results.

Parker has described a method for solving the problem of oversampling certain ray lines during minimal data reconstruction in fan-beam computed tomography with the divergent beam geometry by introducing weights for the oversampled image data. These weights are required to satisfy Equation (1), namely that $$w(\beta,\gamma)+w(\pi+\beta+2\gamma,-\gamma)=1 \quad (1)$$

Parker or Crawford and King ("Computed Tomography Scanning with Simultaneous Patient Translation" Med. Phys. 17, 967–982, 1990 and incorporated herein by reference) give explicit formulae for the weights.

Unfortunately, simple and elegant methods and devices for reconstruction using partial orbits intermediate to the minimal complete data set and the complete orbit have yet to be developed.

SUMMARY OF THE INVENTION

Accordingly, one object of this invention is to provide a method and system for performing CT imaging that does not require highly precise knowledge of the fan angle.

Another object of this invention is to is to provide a method and system for performing CT imaging that does not require precise synchronization of the gantry rotation and X-ray emission.

A further object of this invention is to is to provide a method and system for image reconstruction using partial orbits where the spanned angle is intermediate to the spanned angle of the minimal complete data set orbit and the spanned angle of a complete orbit.

A still further object of the invention is to provide a method and system that provides a tradeoff between suppressing the signal-to-noise ratio and image resolution.

Yet another object of this invention is to provide a method and system for using partial orbits where the spanned angle is intermediate to the spanned angle of the minimal complete data set orbit and the spanned angle of a complete orbit that requires no additional complexity beyond the Parker method for the minimal complete data set in the case of helical cone beam CT.

A further object of the invention is to use as much data as possible for reconstruction while eliminating or minimizing the extent of data extrapolation in the case of a helical cone beam CT.

A yet still further object of this invention is to is to provide comparable methods and systems for use with complete orbits.

These objects can be realized by an image reconstruction method and system that uses a "virtual" fan angle that is equal to the angular rotation about the axis beyond 180° (regardless of the actual fan angle). Alternatively, the "virtual" fan angle is defined as a selected angle that is less than the angular rotation about the axis beyond 180°, but still larger than the angle for collection of the minimal complete data set. The only constraint on the virtual fan angle in both cases is that it is larger than the physical fan angle of the instrument or, in other words, the exposure path is intermediate to the minimal complete data set and a 360° path. The virtual fan angle can be used to calculate weights for the oversampled rays that are used during reconstruction of the interior of objects.

Specifically, a system using such a virtual fan angle will include an X-ray tomograph configured to produce an exposure path of a source about an object of interest that is less than 360° but greater than 180° plus the fan angle. The virtual fan angle can be determined using either the actual angle spanned by such an orbit or a selected smaller angle still larger than the angle necessary to collect the minimal complete data set, and will be used to determine non-uniform weights for the data collected from rays through the orbit and/or to identify the rays to which such weights will be applied. The weighted data can then be used to reconstruct an image according to any of a number of different reconstruction methods.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 5:
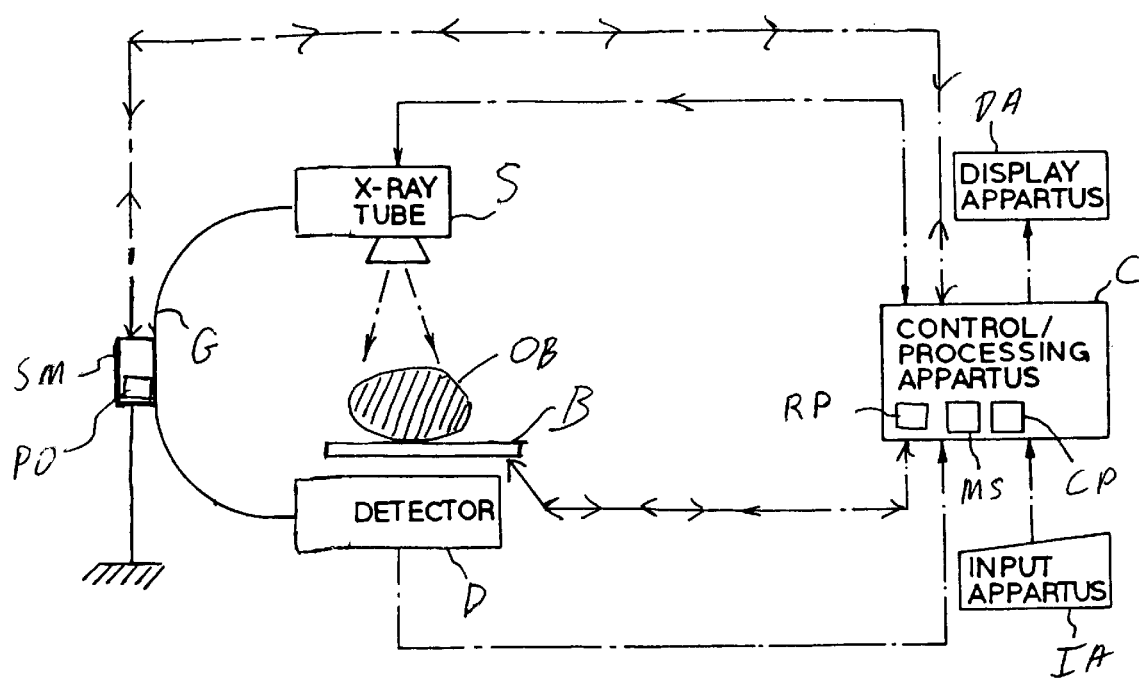
FIG. 5 is a diagram of a C-arm gantry device according one embodiment of the invention.
Figure 6:
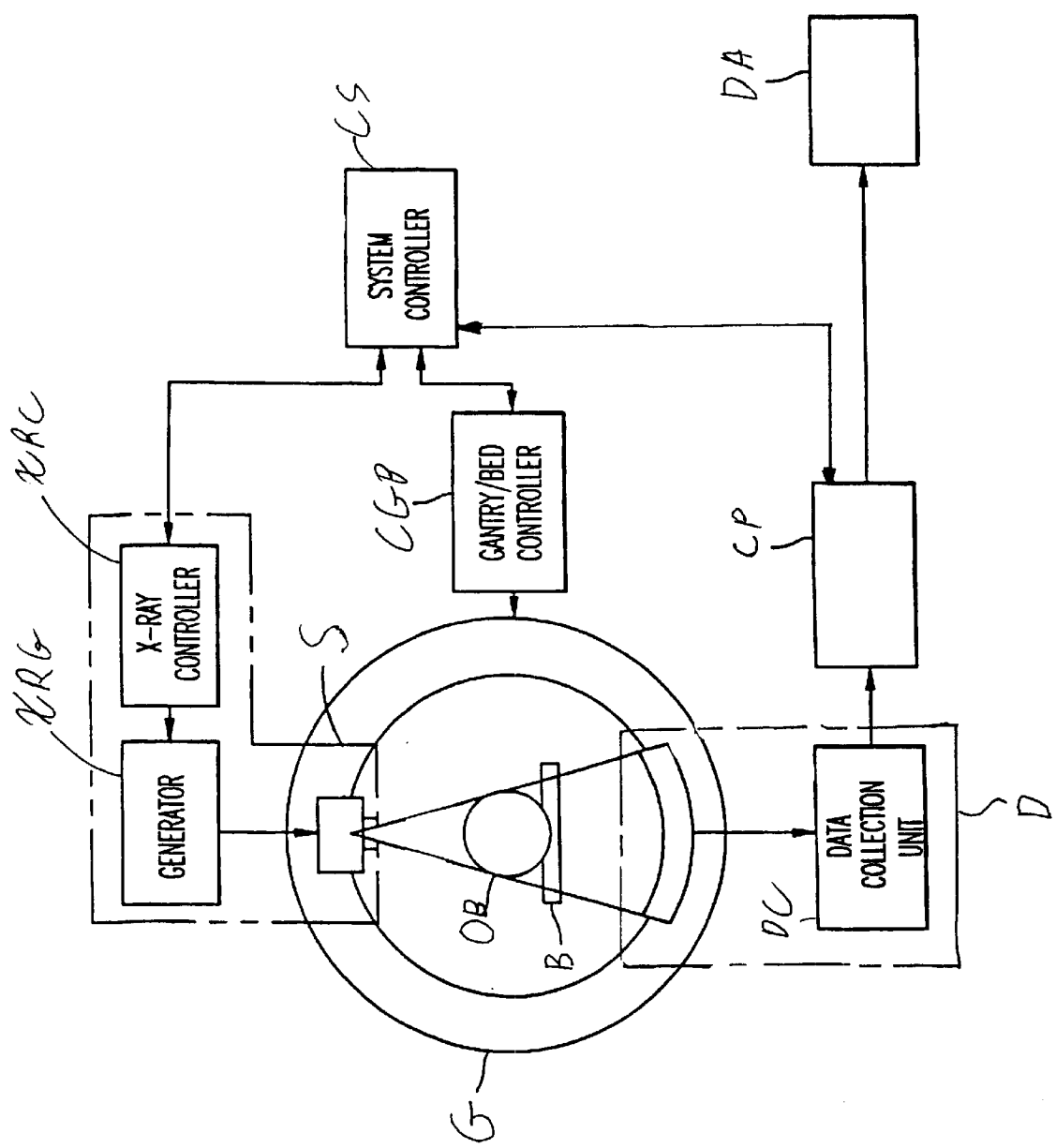
FIG. 6 is a diagram of a helical cone-beam device according to another embodiment of the invention.

Referring now to the drawings, wherein like reference numbers designate identical or corresponding parts throughout the several views, and more particularly to FIGS. 5 and 6 thereof, which illustrate systems for performing CT imaging according to embodiments of the invention, namely a C-arm gantry and a fan-beam or cone-beam CT system, respectively.

Figure 1:
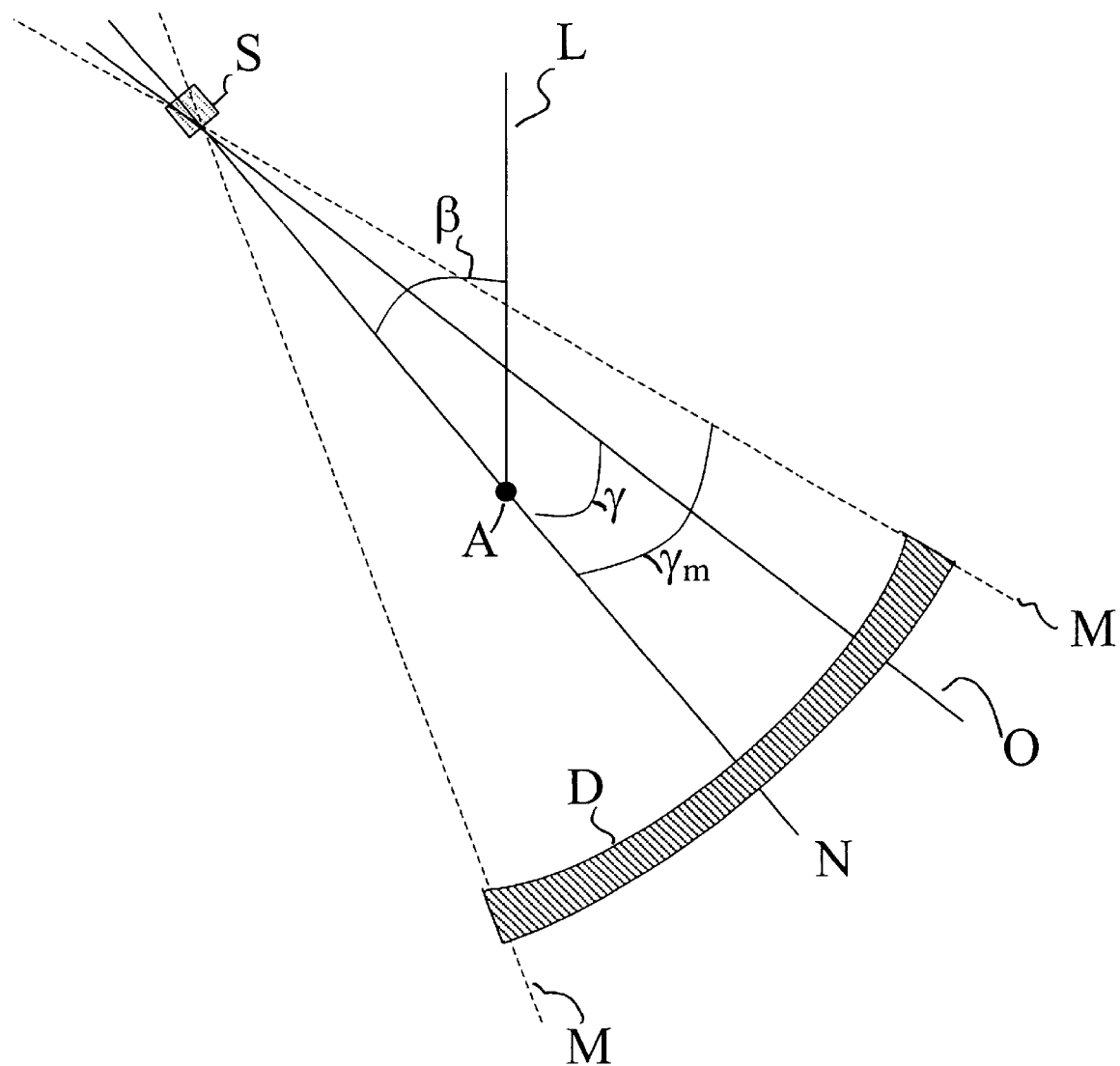
FIG. 1 is a diagram illustrating the coordinate system used to describe the current invention.
Figure 2A:
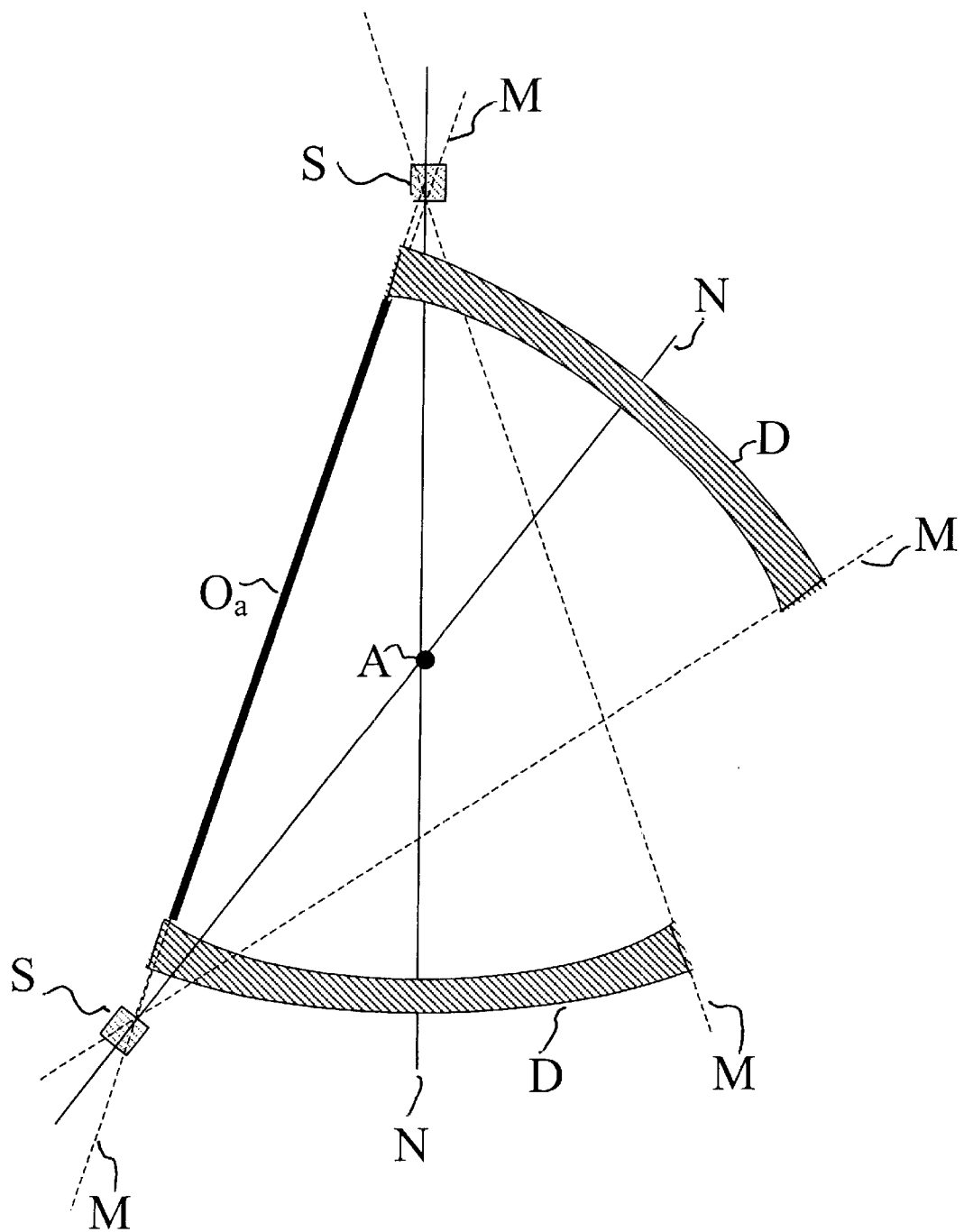
FIGS. 2a–c are diagrammatic illustrations of example rays at various angular positions of the source β that are sampled twice along an orbit that spans an angle equal to or larger than the angle spanned for the collection of a "minimal complete data set" partial orbit.
Figure 2B:
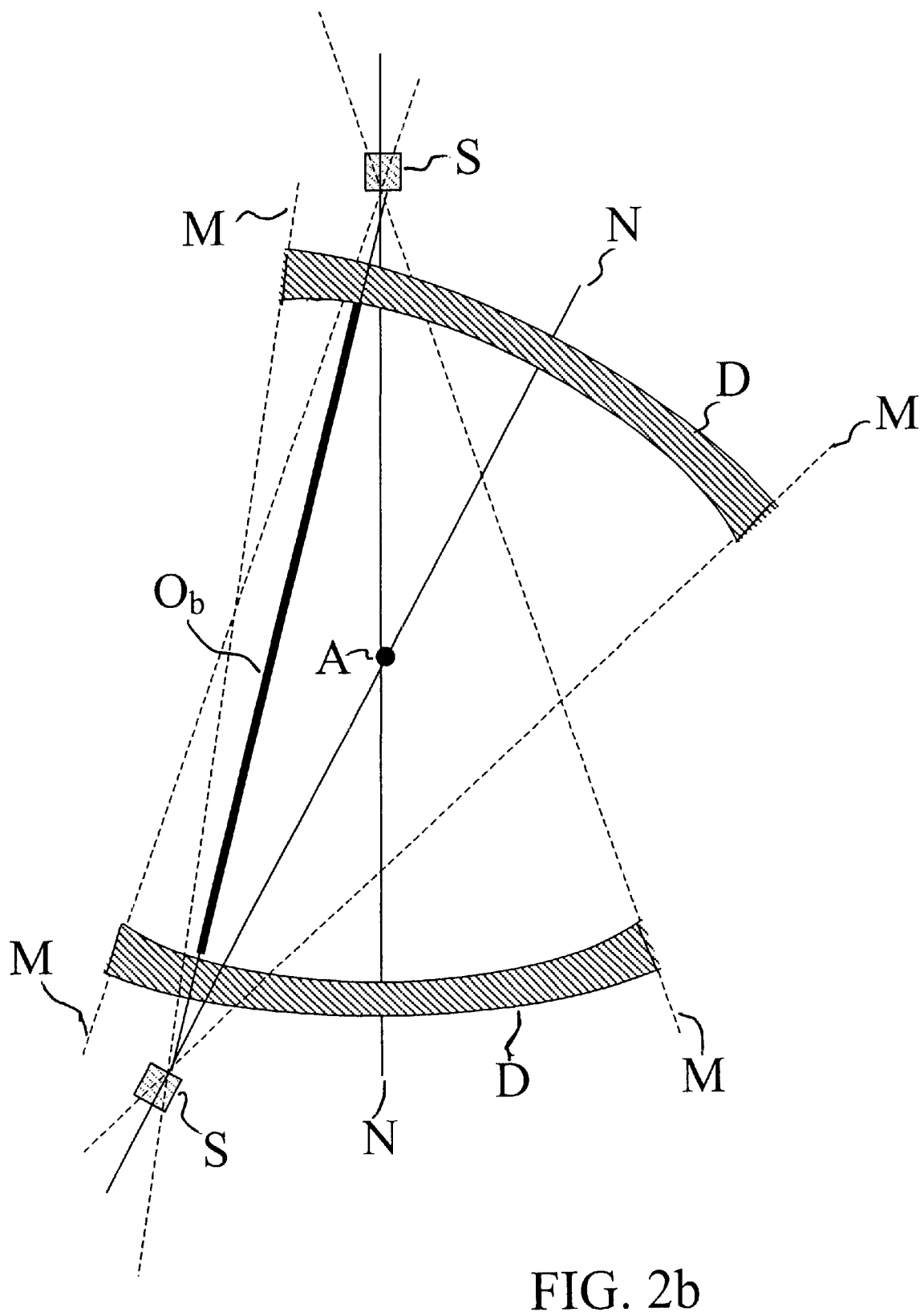
Figure 2C:
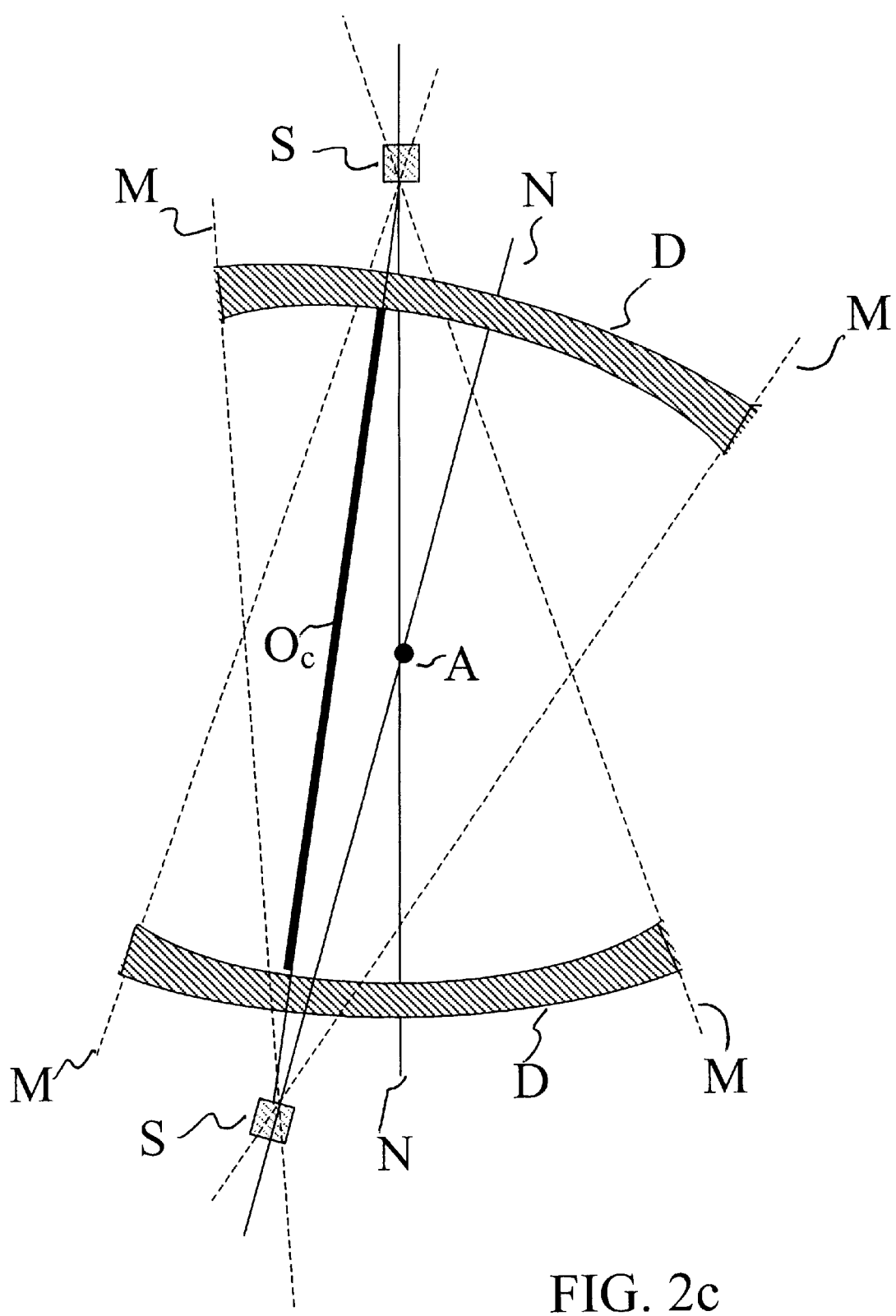
Figure 3:
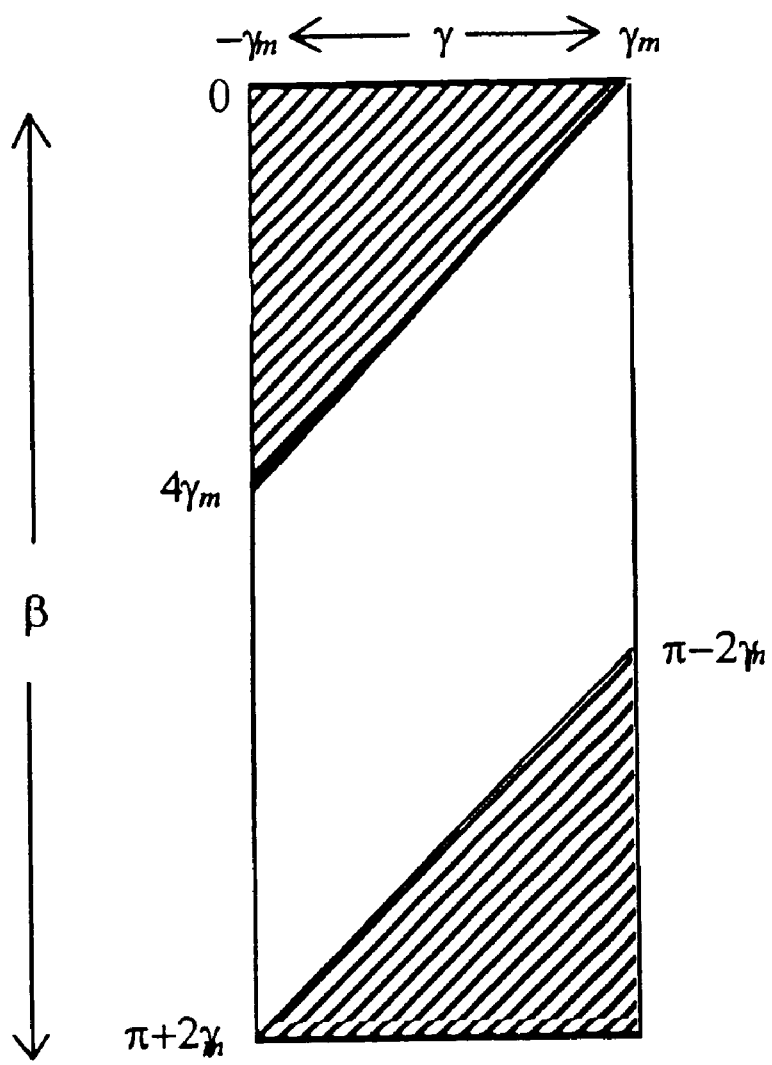
FIG. 3 is a prior art sinogram in Radon space that indicates the angular positions of the source and the fan angles for rays that are sampled twice during the collection of a "minimal complete data set" partial orbit.

A first embodiment of the system according to the invention using fan-beam CT on a diagnostic CT-gantry is shown in FIG. 6. The coordinate system used to describe the current invention is shown in FIG. 1. The projection data measurement system accommodates an X-ray source S that generates a substantially fan-shaped beam of X-ray flux and a linear array X-ray detector D consisting of a linear array of detector elements. X-ray source S and detector D are installed with faces opposing one another on a rotating ring gantry G. An object or patient OB can be placed within the ring gantry G upon a slidably supported bed B. When X-rays generated at source S (or a portion thereof) pass through object OB and are incident upon detector D, detector D transducers the intensity of these X-rays, and the electrical signal is provided to the control/processing apparatus CP after amplification and/or encoding by a data collection unit DC included in detector D. In contrast with FIG. 5, the embodiment of FIG. 6 is provided with a system controller CS external to the control/processing apparatus CP. This system control is responsible for controlling the translation of bed B and movement of gantry G using gantry/bed controller CGB, the firing of source S (in conjunction with X-ray controller XRC and X-ray generator XRG), and the rotation of either bed B about the axis of ring gantry G or the revolution of source S and detector D along an orbit defined by ring gantry G. Data is collected, stored, and manipulated (including weighting and reconstruction) by control/processing apparatus CP. Data from CP can be displayed upon display apparatus DA.

The operation of the first embodiment will now be described. A scan is performed by moving gantry G over a projection range greater than 180° plus the fan angle, and the x-ray data is collected by detector D and fan-beam data stored. See FIG. 7a, step 701. Weights are then determined for the collected rays (step 703), the data is weighted (step 704) and the weighted data is used to reconstruct the image using (step 705). Apparatus C performs the weighting and convolution calculations.

In the present invention, a "virtual" fan angle $\Gamma$ is determined (step 702). The angle may be determined from input data to control the span of the source, or may be selected based upon other parameters, such as the scan pitch, by the processor CP or controller CS. The virtual fan angle $\Gamma$ can be used to describe such intermediate partial orbits. This virtual fan angle $\Gamma$ is used to determine weighting coefficients which are in turned used to weigh certain rays from the collected image data that have been twice-sampled. The weighted rays are themselves used in turn to reconstruct the interior of the object of interest according to any of a number of reconstruction methods. The virtual fan angle $\Gamma$ is given as one half the difference between the range of angular positions of the source and 180° or $$2\Gamma = \Delta\beta \tag{2}$$

Alternatively, the virtual fan angle $2\Gamma$ can be defined using a selected angle smaller than this range but larger than the angle for collection of the minimal complete data set.

Figure 8:
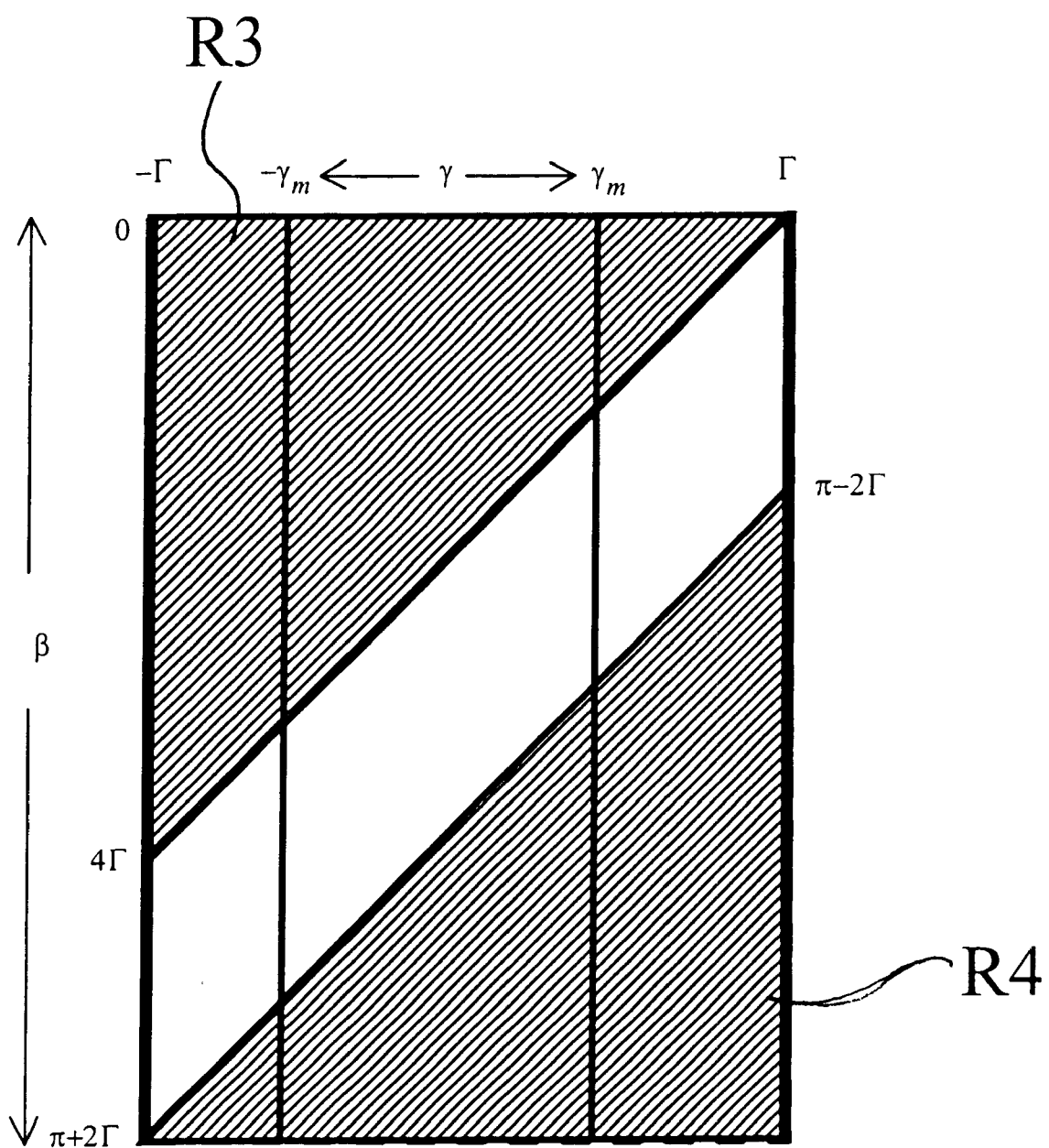
FIG. 8 is a virtual sinogram (graph in Radon space) with the projection range $0<\beta<\pi+\Delta\beta$ and ray-sum angular range within a projection of $-\Gamma \leq \gamma \leq \Gamma$ where $2\Gamma$ is the virtual fan angle of the present invention.

The use of weights determined by using a virtual fan angle results in a virtual sinogram with the projection range $0<\beta<\pi+\Delta\beta$ and ray-sum angular range within a projection of $-\Gamma \leq \gamma \leq \Gamma$ as shown in FIG. 8. This forms a short-scan sinogram with the virtual fan angle of $2\Gamma$. The new Radon space regions $-\Gamma \leq \gamma \leq -\gamma_m$ and $\gamma_m \leq \gamma \leq \Gamma$ for all $\beta$ consists of virtual data values of zero. As long as the real ray-sum values go to zero at $\gamma = +/-\gamma_m$, then applying the virtual fan angle-derived weights to the virtual sinogram with redundant projections gives the correct reconstruction. In an actual implementation, the regions $-\Gamma \leq \gamma < -\gamma_m$ and $\gamma_m < \gamma \leq \Gamma$ can be ignored as long as the weights are generated with $\Gamma$ instead of $\gamma_m$. The weights chosen must meet the relation of Equation (1).

There are two interesting limits with this approach. When $\Delta\beta = 2\gamma_m$, the virtual sinogram reduces to the usual Parker short-scan sinogram. When $\Delta\beta = \pi$, this is a 360° (complete orbit) scan but instead of all the ray-sums weighted equally (with 1), the reflection and weight formulas hold. The two triangular regions R3 defined by the points $(0, -\Gamma)$, $(4\Gamma, -\Gamma)$, and $(0, \Gamma)$ and R4 defined by the points $(\pi+2\Gamma, -\Gamma)$, $(\pi+2\Gamma, \Gamma)$, and $(\pi-2\Gamma, \Gamma)$ in FIG. 8 meet and every ray-sum receives a non-unity weight.

Figure 4:
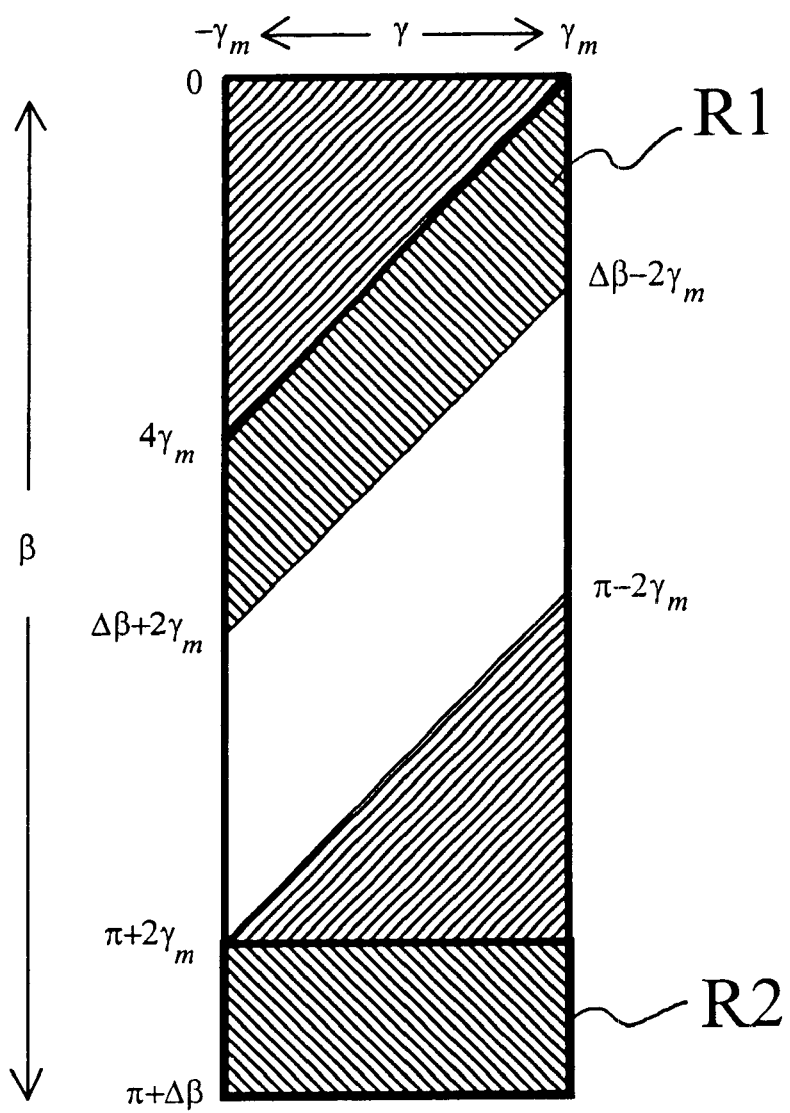
FIG. 4 is a sinogram in Radon space that indicates the angular positions of the source and the fan angles for rays that are sampled twice during the collection of a set of image data using a partial orbit that has a spanned angle intermediate to the spanned angle of a "minimal complete data set" partial orbit and the spanned angle of a complete orbit.

For comparison, FIG. 4 is a sinogram in Radon space that indicates the angular positions of the source and the fan angles for rays that are sampled twice during the collection of a set of image data using a partial orbit that has a spanned angle intermediate to the spanned angle of a "minimal complete data set" partial orbit and the spanned angle of a complete orbit. It becomes apparent that the fraction of twice-sampled rays increases, due both to an increased range $\Delta\beta - 2\gamma_m$ in the angular position of the source $\beta$ and the redundant sampling of previously sampled rays in this increased range $\Delta\beta - 2\gamma_m$.

Any weighting scheme that satisfies Equation (1) may be used. A specific example is $$w = [x(\beta,\gamma)] = 3x^\theta(\beta,\gamma) - 2x'(\beta,\gamma) \tag{3}$$

where $$x(\beta,\gamma) = \begin{cases} \dfrac{\beta}{2\Gamma - 2\gamma} & 0 \leq \beta \leq 2\Gamma - 2\gamma \\ 1 & 2\Gamma - 2\gamma \leq \beta \leq \pi - 2\gamma \\ \dfrac{\pi + 2\Gamma - \beta}{2\Gamma + 2\gamma} & \pi - 2\gamma \leq \beta \leq \pi + 2\Gamma \end{cases} \tag{4}$$

There are numerous conventional methods and devices for performing the reconstruction processing, and such methods may be used in the first embodiment.

Figure 7A:
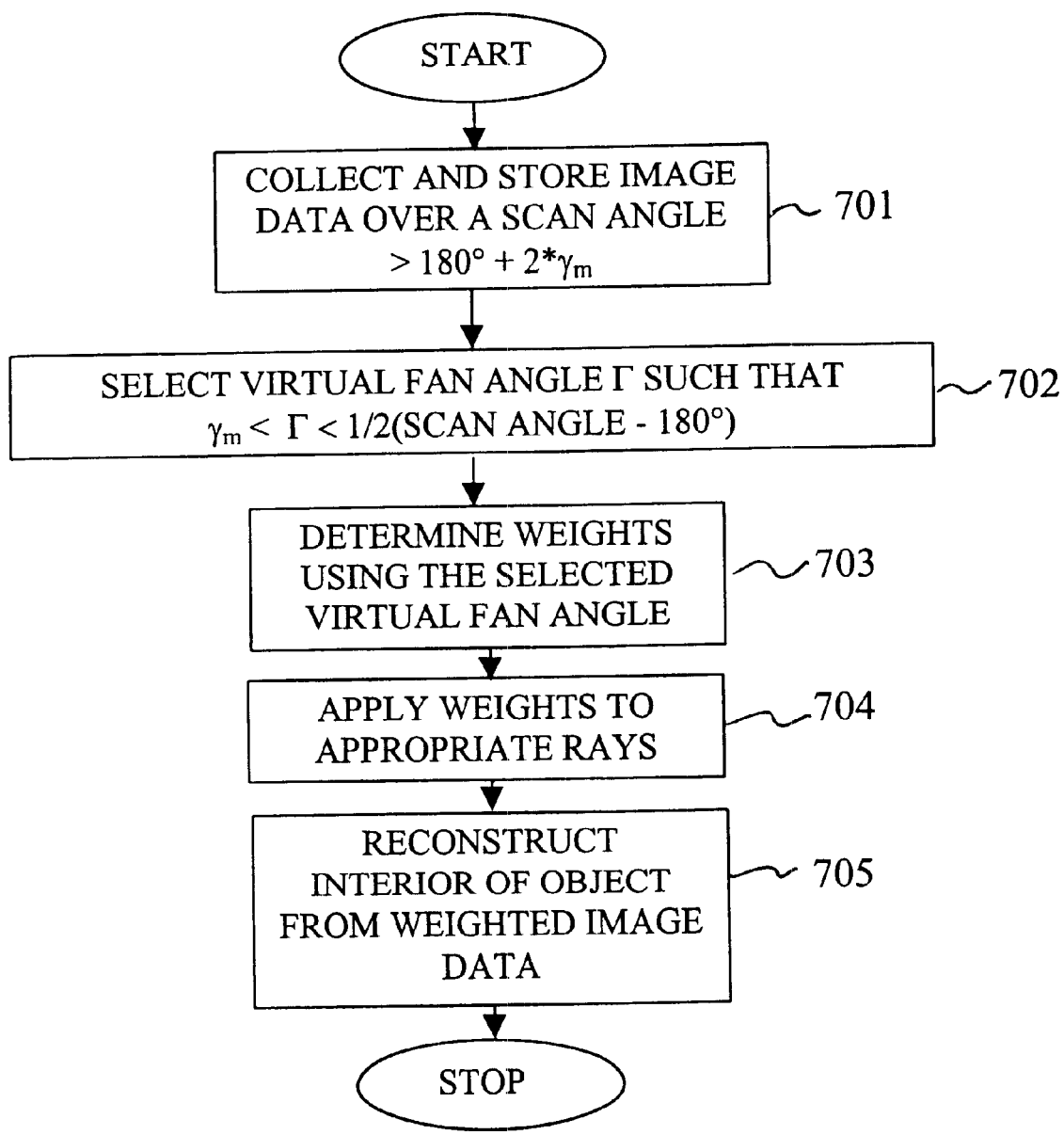
FIGS. 7a and 7b are illustrations of the method according to the invention.
Figure 7B:
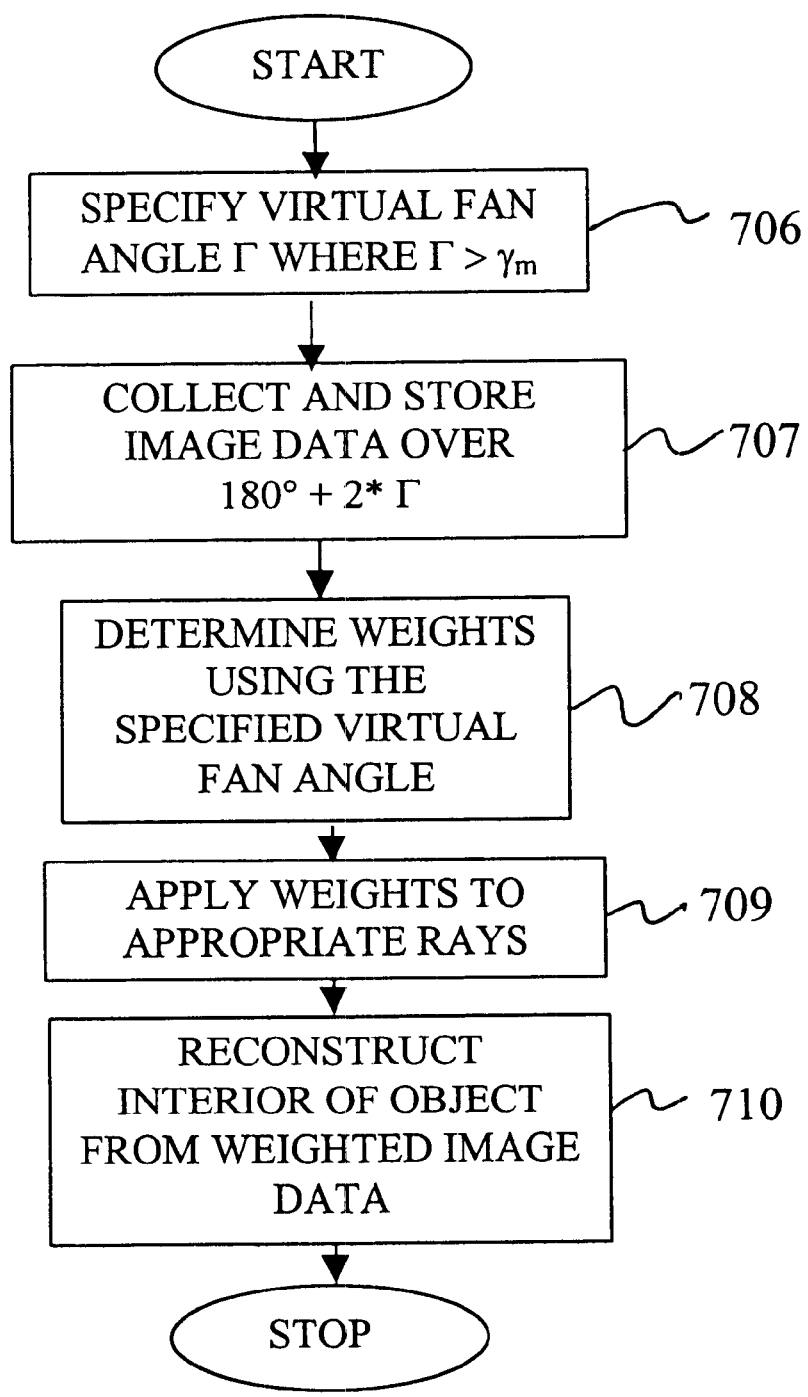

In a modification of the above-described method, shown in FIG. 7b, the virtual fan angle $\Gamma$ is selected (step 706) and the scan is performed over the range of 180° plus 2Γ (step 707). Weights are determined in step 708 and the data is weighted in step 709, as discussed above with respect to FIG. 7a. The image is reconstructed using the weighted data (step 710), also as discussed above.

EXAMPLE 1

The present invention may be applied to traditional single-slice fan-beam CT systems. The invention can be used to provide a tradeoff between image signal-to-noise (SNR) and temporal resolution. Because the views, labeled by β, are sequential in time and all ray-sums for a given view are at the same time, the β-axis and the time-axis are equivalent. Thus, if images have blur or other patent motion artifacts caused by, for example, breathing, heart beating, or by external moving objects that are introduced to the scan field such as a contrast agent or interventional medical devices like biopsy needles, the blur and artifacts content can be controlled by controlling the number of views (the time range) and in reconstruction. The invention allows a tradeoff between SNR and temporal resolution by allowing a virtual fan angle between $2\gamma_m$ and π, the lower and favoring better temporal resolution and the upper and favoring better SNR. The same reasoning that applies in this example can also be applied to the following two examples.

Referring to FIG. 5, a second embodiment of the system according to the invention is illustrated. On a C-shaped gantry G, an x-ray tube S and an x-ray detector D are mounted facing one another. C-arm gantry systems do not have a well determined fan angle and the angular range of the gantry movement is difficult to control, although it is measured. The range of angular positions of the source can be calculated from the difference between the angular positions of the source β in the first and last frame collected. X-rays emitted from source S are transmitted through a object OB on bed B and are detected by detector D. In one embodiment of the invention, bed B is movably supported, with motion controlled by control/processing apparatus C. In another embodiment, bed B includes a position detector and/or accelerometer (neither shown) for control of and confirmation of the execution of motion instructions indicated by control/processing apparatus C.

Detector D generates exposure data, which is transmitted to control/processing apparatus C. As illustrated here, gantry G is rotatably mounted to a support and rotation mechanism SM containing an internal position detector PD for determining the angular position of the gantry, and control of and confirmation of the execution of motion instructions indicated by control/processing apparatus C. The gantry G may alternatively be suspended from a ceiling mount and may be moved along three axes by combining C-arm rotation, C-arm sliding, and support column rotation. In the case of either ceiling or floor mounting, the support and rotation mechanism SM may be moved laterally and longitudinally. C-arm rotation is used to change the angular position of the source (β in FIG. 1), which is in turn determined using a position detector PD. In the embodiment illustrated here, position detector PD is internal to the C-shaped gantry, although it may also be external or implemented in control/processing apparatus C, as described below.

The operation of the system is controlled by a control/processing apparatus C and data input apparatus IA. Device C typically includes a computer or workstation programmed to carry out the necessary functions and calculations for data processing, and handles storing and processing of the exposure data from device D, weighting of the exposure data from detector D, and controls and monitors the operation of the system, including the movement of the C-arm and image acquisition and data storage and receiving position data used to identify the angular position of the source (β in FIG. 1) from position detector PD. Furthermore, control/processing apparatus C performs reconstruction processing to reconstruct images using a reconstruction processor RP from the exposure data. Control/processing apparatus C includes a memory storage device MS for storing, among other things, data provided by detector D. Control/processing apparatus C also includes a processor CP for performing various calculations and performing functions, such as data weighting.

Input apparatus IA allows an operator to input data or commands to operate or monitor the system. Device IA may typically be a graphical interface having a monitor, keyboard and pointing device. A reconstructed image may also be displayed on the display apparatus DA, which may include, e.g., a monitor and/or a printer.

The most common class of devices for determining the angular position of the source are internally-mounted to the support and rotation mechanism SM or other device that actuates the C-arm gantry G that holds the source S. An example is indicated in FIG. 5 as internal position detector PD. A preferred device to measure the angle of rotation is a rotary encoder.

The system of FIG. 5 operates generally in the same manner as shown in FIGS. 7a and 7b. As indicated by FIG. 1, data collection for a number of rays can be performed simultaneously using fan- or cone-beam CT. The virtual fan angle Γ may be chosen beforehand, and the scan may cover (or exceed) this angular range, or a scan may be performed and Γ may be chosen afterwards. There are numerous methods and devices for performing the reconstruction processing. For example, the method described by Feldkamp Davis, and Kress ("Practical Cone-Beam Algorithm", J. Opt. Soc. Am. A1, 612–619, 1984) can be used with the virtual cone-beam angle-weighted rays for the reconstruction of the interior of objects of interest.

EXAMPLE 2

The present invention may be applied to C-arm gantries systems such as the Toshiba CAS8000V and CAS10A/AX. Both are digital subtraction angiography (DSA) imagers: the first is ceiling mounted, the latter floor mounted. Both these gantries record the angle (to nearest tenth of a degree) for each frame (a TV-like snapshot of the patient that is digitized) that is collected. Thus, when reconstruction is started, the angles for first and last frame collected are known. This difference is the range and is 2Γ+π. In the Toshiba systems described above, three computers are actually used. One handles the data acquisition, one handles CT reconstruction and the third handles the display.

The method according to the invention allows redundant data to be included in CT reconstructions of fan- and cone-beam data without introducing additional complexity to a method such as described by Parker. It should be noted that while the above discussion has been simplified to explain fan-beam exposure, it is equally applicable to cone-beam exposure. In cone-beam exposure, the beam is collimated to have a rectangular cross-section to expose essentially the two-dimensional array of detector elements with a fan angle as defined in FIG. 1.

A third embodiment of the system according to the invention using helical cone-beam CT on a diagnostic CT-gantry is shown in FIG. 6. In this case, the projection data measurement system accommodates an X-ray source S that generates a substantially cone-shaped beam of X-ray flux and a two-dimensional array X-ray detector D consisting of an area array of detector elements, typically 4 rows of detector elements.

The cone-beam system of FIG. 6 also operates generally in the same manner as shown in FIGS. 7a and 7b. As indicated by FIG. 1, data collection for a number of rays can be performed simultaneously using cone-beam CT. The virtual fan angle $\Gamma$ may be chosen beforehand, and the scan may cover (or exceed) this angular range, or a scan may be performed and $\Gamma$ may be chosen afterwards.

For helical cone-beam on a diagnostic CT gantry, the present invention allows more data to be used without extrapolating to where no data exists. For example, consider that voxel represents a tiny volume of the object of interest. Many conventional algorithms call for backprojection of the ray-sum from the focal spot of the x-ray source position through the voxel to the detector. Different voxels are in the cone-beam differently. An algorithm that tries to backproject from one source position through all of the voxels (of a given slice) contains ray-sums that hit and ray-sums that miss the detector, the position that hit and miss depends on helical pitch and FOV. FOV stands for "field of view." In the present invention, more dose data is used, keeping extrapolation to a minimum or eliminating it altogether.

EXAMPLE 3

The invention is applied to cone-beam multi-slice CT apparatus having a maximum fan angle of 49.2°. The helical pitch will affect the selection of $\Gamma$. Let $\beta_1(x,y)$ be the gantry angle when the pixel at x,y enters the cone-beam, and $\beta_2(x,y)$ be the gantry angle when the pixel at x,y leaves the cone-beam. If $\beta=0$ is defined as the gantry angle when the slice is aligned with the focal spot, then all $\beta_1$'s are less than 0 and all $\beta_2$'s are greater than zero. Because of the circular symmetry of the image, the magnitude of the maximum $\beta_1$ is the same as the minimum $\beta_2$, and vice-versa, although not at the same pixel x,y.

The virtual fan angle (2$\Gamma$) may be based upon the angular range that the isocenter pixel (x,y=0,0) is in the cone beam. Artifacts may result in those regions of the slice that are in the cone beam for a smaller gantry angular range than isocenter because of data extrapolation. Here, the fan angle should be selected such that data extrapolation is not necessary. This gives the following conditions for 2$\Gamma$:

$$2\Gamma = \begin{cases} 180° & \min(\beta'_\theta s) > 180° \\ 2 \times \min(\beta'_\theta s) - 180° & 114.6° \le \min(\beta'_\theta s) \le 180° \\ 49.2° & \min(\beta'_\theta s) < 114.6° \end{cases} \quad (5)$$

for each FOV field-of-views in normal slice direction and helical pitch. Note that 114.6° satisfies 49.2°=2×114.6°−180°, where 49.2° is the actual fan angle of the scanner. In order not to have data extrapolation, 2$\Gamma$ must be greater than 49.2°. The following table on summarizes these findings for the five FOV's of the scanners and three likely helical pitches. Entries in italics will have data extrapolations for some pixels in the reconstructed image.

| FOV (mm) | Helical Pitch | 2$\Gamma$ |
|---|---|---|
| 500 | 0.625 | 156° |
|  | 1.0 | 49.2° |
|  | 1.25 | 49.2° |
| 400 | 0.625 | 180° |
|  | 1.0 | 60° |
|  | 1.25 | 49.2° |
| 320 | 0.625 | 180° |
|  | 1.0 | 88° |
|  | 1.25 | 49.2° |
| 240 | 0.625 | 180° |
|  | 1.0 | 108° |
|  | 1.25 | 50° |
| 180 | 0.625 | 180° |
|  | 1.0 | 126° |
|  | 1.25 | 64° |

Helical pitch is determined as table travel during one revolution of the source divided by the full width of the detector as projected as isocenter.

In the case of reconstructing a 500 mm object scanned at a helical pitch of 1, there is no data extrapolation for any pixel less than 200 mm from isocenter (because the entry for 2$\Gamma$ for the 400 mm FOV, helical pitch of 1, is greater than 49.2°). Similarly, at a pitch of 1.25, there is no data extrapolation for any pixel less than 120 mm from isocenter; however, some pixels more than 120 mm from isocenter will use data extrapolations.

In this example, the method according to the invention should be less noisy. Compared to half-scanning (HS) the improvement is given by $$\frac{\text{Noise with HS}}{\text{Noise with MHS}} = \sqrt{\frac{180 + 2\Gamma}{180 + 49.2}}. \quad (6)$$

However, reconstruction time is longer by $$\frac{360}{180 + 2\Gamma}. \quad (7)$$

because of the additional views to backproject. To keep scaling consistent, the final image may require an additional scale factor of $$\frac{180 + 2\Gamma}{180 + 49.2} \quad (8)$$

The present invention provides for selecting a virtual angle based upon a helical pitch providing desired image characteristics such as image contrast of subtle features in the image.

The present invention may also be implemented as software to perform the various functions and calculations described above. The software is stored in the processor C in FIG. 5 or in the system controller CS or processor CP of FIG. 6. The software may be installed on a disk to implement the invention as a computer program product.

Obviously, numerous modifications and variations of the present invention are possible in light of the above teachings. For example, the present invention may be implemented in the form of software stored on a recording medium, i.e., a computer program product. It is therefore to be understood that within the scope of the appended claims, the invention may be practiced otherwise than as specifically described herein.

What is claimed as new and desired to be secured by Letters Patent of the United States is:

1. A method for reconstructing an image of a subject, comprising:
obtaining x-ray exposure data along a path about said subject spanning less than 360° and more than 180° plus a maximum fan angle of exposure;
determining a virtual fan angle;
weighting said exposure data based upon said virtual fan angle; and
reconstructing said image from weighted exposure data.

2. A method as recited in claim 1, comprising:
obtaining said exposure data before determining said virtual fan angle.

3. A method as recited in claim 1, comprising:
exposing said subject over a path spanning 180° plus said virtual fan angle.

4. A method as recited in claim 1, comprising:
weighting said exposure data using weights w satisfying:

$$w(\beta,\gamma)+w(\pi+\beta+2\gamma,-\gamma)=1$$

where:
$\beta$ is an angular position at which said exposing step is performed, and
$\gamma$ is a channel angle.

5. A method as recited in claim 1, comprising:
helically scanning said subject with a cone-beam of x-rays at a helical pitch.

6. A method as recited in claim 5, comprising:
selecting said virtual fan angle based upon said helical pitch.

7. A method as recited in claim 1, comprising:
determining said virtual fan angle as greater than said maximum fan angle.

8. A method as recited in claim 1, comprising:
constructing a virtual sinogram having a projection range of $0<\beta<\pi+\Delta\beta$ and ray-sum angular range within a projection of $-\Gamma\leq\gamma\leq\Gamma$, where
$\beta$ is an angular position at which said exposing step is performed,
$\gamma$ is a fan angle, and
$\Gamma$ is said virtual fan angle.

9. A method as recited in claim 1, wherein said weighting non-uniformly step further comprises:
identifying rays that have been sampled more than one time.

10. A method as recited in claim 1, wherein said weighting non-uniformly step further comprises:
determining a fan angle and an angular position of said source for rays obtained as said exposure data; and
identifying rays that have been sampled more than one time.

11. The method as recited in claim 1, wherein said weighting non-uniformly step further comprises:
determining a fan angle and an angular position for each of rays obtained as exposure data; and
deriving a weight for each ray obtained as exposure data based upon at least one of said fan angle, said angular position of each ray, and said virtual fan angle; and
multiplying a value of said each ray obtained as exposure data by said weight for each ray.

12. A method as recited in claim 1, wherein said determining said virtual fan angle comprises:
selecting an angle less than an angular range of said path;
setting said virtual fan angle as equal to one half a difference between said selected angle and 180°.

13. A method as recited in claim 1, comprising:
exposing said subject to a fan-beam of x-rays;
selecting said virtual fan angle based upon a tradeoff between temporal resolution and signal-to-noise ratio.

14. A computed tomography system, comprising:
an x-ray source;
an x-ray detector disposed to receive x-rays emitted from said source;
a controller connected to said source and said detector adapted to control said source to expose a subject to x-rays to obtain exposure data along a path about said subject spanning less than 360° and more than 180° plus a maximum fan angle;
a virtual fan angle determining device connected to said controller;
a virtual fan angle weighting device connected to said controller; and
a reconstruction processor connected to said controller.

15. A system as recited in claim 14, wherein:
said x-ray source comprises one of a fan-beam and cone-beam x-ray source;
said x-ray source and said x-ray detector are mounted on a circular gantry;
said subject is disposed on a moveable bed; and
said controller adapted to control said gantry and said bed to effect respective fan-beam scanning and helical cone-beam scanning.

16. A system as recited in claim 14, comprising:
said x-ray source comprises one of a fan- and cone-beam x-ray source;
said x-ray source and said x-ray detector are mounted on a C-arm gantry; and
said controller adapted to control said gantry to perform said exposing of said subject.

17. A system as recited in claim 14, comprising:
means for measuring an angular span of said source;
said virtual angle determining device determining a virtual angle using the angular span;
said weighting device determining weights using the virtual fan angle.

18. A system as recited in claim 14, comprising:
said weighting device weighting said exposure data using weights w satisfying:

$$w(\beta,\gamma)+w(\pi+\beta+2\gamma,-\gamma)=1$$

where:
$\beta$ is an angular position at which said exposing step is performed, and
$\gamma$ is a fan angle.

19. A system as recited in claim 14, comprising:
said virtual fan angle determining device determining said virtual fan angle as one half the difference between an angular length of said path and 180°.

20. A system as recited in claim 14, comprising:
said virtual fan angle determining device determining said virtual fan angle as greater than said maximum fan angle.

21. An X-ray computed tomography system, comprising:

a multi-slice helical scanning unit;

an x-ray source configured to expose a subject to x-rays;

an x-ray detector configured to receive the x-rays emitted from said source and passed through the subject;

an acquisition device configured to obtain projection data based on an output of said x-ray detector;

a reconstruction device configured to reconstruct a CT image from the projection data spanning less than 360° and more than 180° plus fan angle and determine a span based on a helical scanning pitch.

22. An apparatus according to claim 21, wherein the projection data spans 270°.

23. An apparatus according to claim 21, further comprising:

a determination device to determine a span; and a weighting device, connected to said acquisition device, for weighting the projection data based on the span determined by said determination device.

24. An apparatus according to claim 21, further comprising:

said reconstruction device using one of an Extended Half-scanning reconstruction function, a Half-scanning reconstruction function, and a Full-scanning reconstruction function, the Extended Half-scanning reconstruction function reconstructing the CT image based on the projection data of spanning less than 360° and more than 180° plus fan angle, the Half-scanning reconstruction function reconstructing the CT image based on the projection data of spanning 180° plus fan angle, the Full-scanning reconstruction function reconstructing the CT image based on the projection data of spanning 360°.

25. An apparatus according to claim 21, wherein said determination device determines a span based on a field of view, the field of view selected from size of the subject.

26. An X-ray computed tomography system, comprising:

a data acquisition device, configured to acquire projection data by scanning an object;

a reconstruction device, configured to reconstruct a CT image from the projection data, including:

a virtual fan angle generator configured to generate a virtual fan angle, wherein the virtual fan angle is different from a real fan angle for scanning the object;

a weighting unit configured to weight the projection data by an weighting function, wherein the weighting function is determined based on the virtual fan angle; and a reconstructing unit configured to reconstruct the CT image from the weighted projection data.

27. A system as recited in claim 26, wherein:

said data acquisition device acquires the projection data by helically scanning, wherein the helical scanning rotates an X-ray source while the object is moving along a body axial direction of the object; and said virtual fan angle generator generates the virtual fan angle based on a helical pitch of the helical scanning.

* * * * *